US010048392B2

(12) United States Patent
Long

(10) Patent No.: US 10,048,392 B2
(45) Date of Patent: Aug. 14, 2018

(54) NUCLEAR IMAGING SCANNER WITH EVENT POSITION-IDENTIFYING ACCELEROMETERS

(75) Inventor: James Mark Long, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1716 days.

(21) Appl. No.: 13/427,018

(22) Filed: Mar. 22, 2012

(65) Prior Publication Data

US 2012/0179034 A1 Jul. 12, 2012

Related U.S. Application Data

(63) Continuation-in-part of application No. 12/070,751, filed on Feb. 21, 2008, now abandoned.

(51) Int. Cl.
| G01T 1/20 | (2006.01) |
| G01T 1/24 | (2006.01) |
| G01T 1/29 | (2006.01) |
| A61B 6/03 | (2006.01) |

(52) U.S. Cl.
CPC .......... *G01T 1/2985* (2013.01); *A61B 6/037* (2013.01)

(58) Field of Classification Search
CPC ...................................... A61B 6/547

USPC .......... 250/252.1, 362, 370.08, 395
See application file for complete search history.

(56) References Cited

U.S. PATENT DOCUMENTS

| 4,980,552 A | 12/1990 | Cho et al. |
| 6,092,928 A | 7/2000 | Mattson et al. |
| 7,750,311 B2 | 7/2010 | Daghighian |
| 2009/0032714 A1 | 2/2009 | Peter et al. |
| 2009/0152471 A1* | 6/2009 | Rousso et al. ........... 250/363.04 |

* cited by examiner

*Primary Examiner* — David Porta
*Assistant Examiner* — Carolyn Igyarto

(57) ABSTRACT

Methods, systems, and computer-readable mediums are provided that determine the angular orientation of detectors and detector electronic assemblies ("DEAs"). In various embodiments, the orientation of detectors/DEAs (in the ring) is determined with respect to other detectors/DEAs in the ring, the orientation of the detectors/DEAs with respect to a patient bed, or the orientation of the detectors/DEAs with respect to Earth's gravitational field. In another embodiment, a nuclear medical imaging system has one or more detector units arranged around or that can be swept around a patient bed. Each of the detector units includes an angular orientation-sensing accelerometer. By determining angular orientation of the detector from signals outputted by the accelerometer, the circumferential position of the detector relative to the patient bed can be determined. That information is used in conjunction with information about detected events to construct an image of an organ or tissue mass of interest.

6 Claims, 5 Drawing Sheets

| 302 | 304 | 306 | 308 | 310 |
|---|---|---|---|---|
| $302_0$ | $304_0$ | $306_0$ | $308_0$ | $310_0$ |
| $302_1$ | $304_1$ | $306_1$ | $308_1$ | $310_1$ |
| $302_2$ | $304_2$ | $306_2$ | $308_2$ | $310_2$ |
| $302_3$ | $304_3$ | $306_3$ | $308_3$ | $310_3$ |
| $302_4$ | $304_4$ | $306_4$ | $308_4$ | $310_4$ |
| $302_5$ | $304_5$ | $306_5$ | $308_5$ | $310_5$ |
| $302_6$ | $304_6$ | $306_6$ | $308_6$ | $310_6$ |
| $302_7$ | $304_7$ | $306_7$ | $308_7$ | $310_7$ |
| $302_8$ | $304_8$ | $306_8$ | $308_8$ | $310_8$ |
| $302_9$ | $304_9$ | $306_9$ | $308_9$ | $310_9$ |
| $302_{10}$ | $304_{10}$ | $306_{10}$ | $308_{10}$ | $310_{10}$ |
| $302_{11}$ | $304_{11}$ | $306_{11}$ | $308_{11}$ | $310_{11}$ |

FIG. 3

NUCLEAR IMAGING SCANNER WITH EVENT POSITION-IDENTIFYING ACCELEROMETERS

CROSS-REFERENCE TO RELATED APPLICATIONS

This is a continuation-in-part of U.S. patent application Ser. No. 12/070,751, filed Feb. 21, 2008.

BACKGROUND

Field of the Invention

Embodiments of the present invention generally relate nuclear imaging and more specifically to systems, methods, apparatuses, and computer-readable mediums for determining the orientation/location of immobile detectors/detector electronic assemblies.

Description of the Related Art

In PET imaging, for example, positrons are emitted from a radio-pharmaceutically doped organ or tissue mass of interest. The positrons combine with electrons and are annihilated and, in general, two gamma photons which travel in diametrically opposite directions are generated simultaneously upon that annihilation. Opposing crystal detectors, which each scintillate upon being struck by a gamma photon, are used to detect the emitted gamma photons. By identifying the location of each of two essentially simultaneous gamma interactions as evidenced by two essentially simultaneous gamma emissions from a positron annihilation event, a line in space along which the two gamma photons have traveled (a "line of response," or "LOR") can be determined, from which the location of the original positron annihilation event can be calculated. The LORs associated with many million annihilation events with the detectors are calculated and "composited" to generate an image of the organ or tissue mass of interest, as is known in the art.

Conventionally, an array of PET crystal detectors may be arranged circumferentially all the way around a bed on which the patient lies during the scan, with the bed oriented horizontally and the "ring" of detectors oriented in a vertical plane with the bed extending axially through the center of the ring. In such a case, with detectors completely surrounding the patient bed, the detectors remain stationary. (The bed may move longitudinally to image different regions of interest of the patient's body).

There are scanning systems where detectors and detector electronic assemblies ("DEAs") rotate on a gantry, other scanning systems where the detectors and DEAs move intermittently, and yet other systems where the detectors and DEAs remain immobile.

In systems where the detectors remain immobile (i.e., stationary and not intended to move), it is still necessary to know the position in space of each detector (i.e., by digitally "tagging" or identifying each PET interaction event with its associated detector position) so that the LORs can be constructed.

Even though the detectors remain stationary, there are times when the scanner system is relocated to a different location and the spatial location of a detector(s) is changed as a result. There are also times when detectors are replaced. These movements result in the detectors/DEAs having a possibly unknown angular orientation and location.

In general, the detector position can be determined if the angular orientation in space of the detector is known, since each detector around the ring of detectors will have a unique angular orientation. Current schemes set in hardware—usually by use of DIP switches—the circumferential position of each of the acquiring detector's electronics, thereby providing a basis by means of which individual detector pixels may be encoded. DIP switches are used to determine a detector electronic assembly ("DEA") location with respect to other detector electronic assemblies and a patient bed. The DIP switches are located on a circuit board of the DEA. DIP switches, however, may require manual setting and can be difficult to access. In addition, DIP switches require time to set and can be easily set to an incorrect setting.

Other PET imaging systems, on the other hand, use fewer detectors, and the detectors do not completely encircle the patient bed. For example, PET systems are known which use just two opposing detectors that are supported by a gantry, and the detectors are rotated by the gantry, e.g., through 180° each, so as to acquire a full 360° sweep of the patient. Other types of imaging systems such as SPECT imaging systems, as well as others, may use even less detectors, i.e., a single detector, and also acquire a fully swept image by rotating the detector around the patient, e.g., through a full 360°.

These non-fully-encircling systems (PET, SPECT, and others) also rely on knowing the position of the detector in space in order to construct LORs or otherwise generate an image of the patient. In such rotating systems, the detector position in space is typically determined by determining the rotational position of the gantry, which requires geared linkages and/or encoders. "Play" between system components can, however, cause inaccuracies in the detector positions determined by such means.

Accordingly, improved instrumentalities for determining the position of nuclear imaging detector(s) and DEAs, in a system in which the detectors and DEAs remain immobile (i.e., stationary); and the initial starting position (in rotating systems), is desirable.

SUMMARY

According to various embodiments of the invention, a nuclear medical imaging system has one or more detector units arranged around or that can be swept around a patient bed. Each of the detector units includes an angular orientation-sensing accelerometer. By determining angular orientation of the detector, the circumferential position of the detector relative to the patient bed can be determined That information is used in conjunction with information about detected events to construct an image of an organ or tissue mass of interest.

In particular, according to one aspect of the invention, a nuclear medical imaging system is provided, which includes at least one detector unit that is sensitive to radiation emitted by a radio-pharmaceutically doped organ or tissue mass of interest; and an angular orientation-sensing member mounted on the detector unit.

According to another aspect of the invention, a method of encoding scintillation events detected by a radiation detector includes providing an angular orientation value from an angular orientation member associated with the radiation detector, associating the angular orientation value with information concerning a detected scintillation event from the radiation detector, and transmitting the associated information to a processor.

In another aspect of the invention, a system is provided that includes a plurality of immobile detector electronics assemblies ("DEAs"). The system also includes a plurality of groups of immobile detectors, such that each group is connected to a respective DEA. The system has plurality of accelerometers, such that each accelerometer is connected to a respective DEA. Each accelerometer is adapted to transmit a signal indicative of at least one of an orientation of respective DEA connected thereto with respect to other DEAs, the orientation of the respective DEA with respect to a patient bed, and the orientation of the respective DEA with respect to Earth's gravitational field.

In other embodiments of the invention computer-readable mediums and methods are provided which determine the orientation of DEAs and/or detectors. For example, exemplary method receives data from a plurality of accelerometers. The accelerometers can be mounted to the DEAs or to the detectors. Each accelerometer transmits data indicative of the orientation of the device (i.e., the DEAs or detectors) mounted thereto. The transmitted data is compared to predefined location parameters to determine a location of the device (i.e., the DEAs or detectors) mounted thereto.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3 depicts an exemplary look-up table in accordance with embodiments of the invention;

To facilitate understanding, identical reference numerals have been used, wherever possible, to designate identical elements that are common to the figures.

DETAILED DESCRIPTION

In the following description, numerous specific details are set forth to provide a more thorough understanding of the invention. As will be apparent to those skilled in the art, however, various changes using different configurations may be made without departing from the scope of the invention. In other instances, well-known features have not been described in order to avoid obscuring the invention. Thus, the invention is not considered limited to the particular illustrative embodiments shown in the specification and all such alternate embodiments are intended to be included in the scope of the appended claims.

Figure 1:
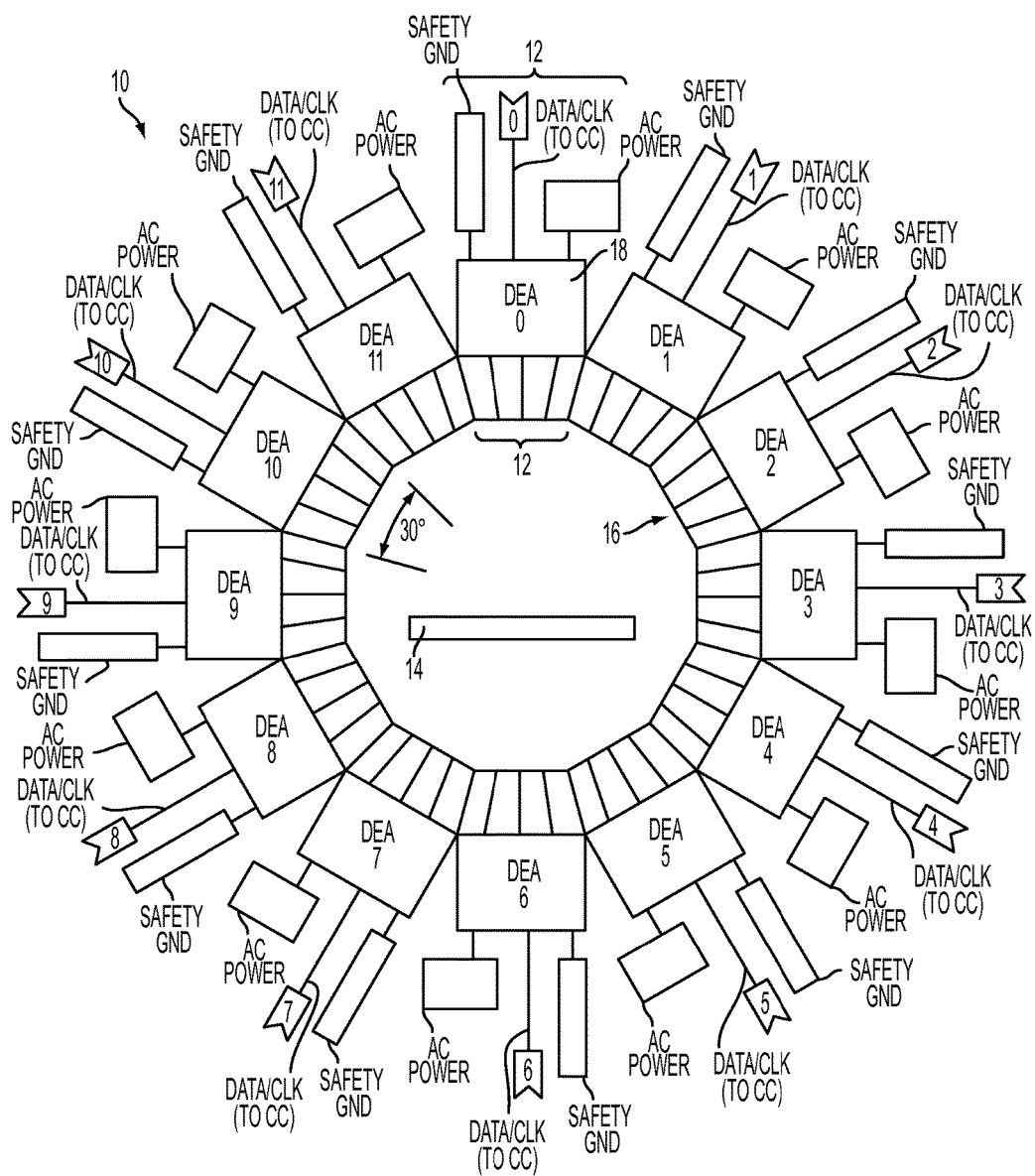
FIG. 1 is a schematic view of a completely encircling PET detector employing angular orientation accelerometers according to embodiments of the invention.

FIG. 1 depicts a PET detector system 10 according to one embodiment of the invention. The system 10 is of the type described above in which a ring of detector units 12 encircles a patient bed 14. For example, as illustrated, twelve detector units 12 (identified as 0 through 11) may be provided, with each detector unit 12 having a 30° field of view. As is known in the art, each detector unit 12 may include a pixelated detector crystal and may, depending on the specific construction of the unit 12, include a set of photomultiplier tubes or other photosensors. The detector crystals (and photomultiplier tubes) are designated generally (and collectively) by reference numeral 16.

As further illustrated in the FIG. 1, each detector unit 12 includes a direct-encoding, DC accelerometer 18 (DEA) (broadly referred to as an angular orientation-sensing member). Such accelerometers are generally known in the field and typically include a pair of orthogonally arranged sensing elements by means of which the angle of inclination of the accelerometer relative to Earth's gravitational field can be determined. Thus, by measuring the angle of inclination of the detector unit 12, the location of the detector unit 12 can be determined, and that location information can be tagged to each event detected by the detector unit, for which the information concerning the detector unit is sent to the imaging system processing computer (not illustrated).

For example, the top detector unit 12 (identified as the 0 detector unit in FIG. 1) has a detector orientation of 180° (facing straight down); thus, any detected event that occurs at the topmost detector unit 0 is tagged with an orientation of 180°. Similarly, for a twelve-unit system as shown, the next detector unit 12 in the clockwise direction (identified as 1 in FIG. 1) will have an orientation of 210°; the next detector unit 2 will have an orientation of 240°; and so on around the detector system. Thus, the detected events from all detector units 12 can be compiled along with the associated detector orientations, and the LORs can be generated by pairing essentially simultaneous events that have associated detector orientations that are 180° apart from each other.

In an alternative arrangement (not illustrated), only one or two detector units are provided, which do not completely encircle the patient bed but which are swept around the patient as described above. The detector(s) in such an arrangement would also include an orientation-sensing accelerometer, by means of which the position in space of the detector can be determined and hence the angular location of the detector. As above, with such a system (particularly a PET system with two opposing detector units), all detected events can be compiled and paired based on opposing detector locations, together with the actual angular orientation of the opposing detectors in space.

Figure 2:
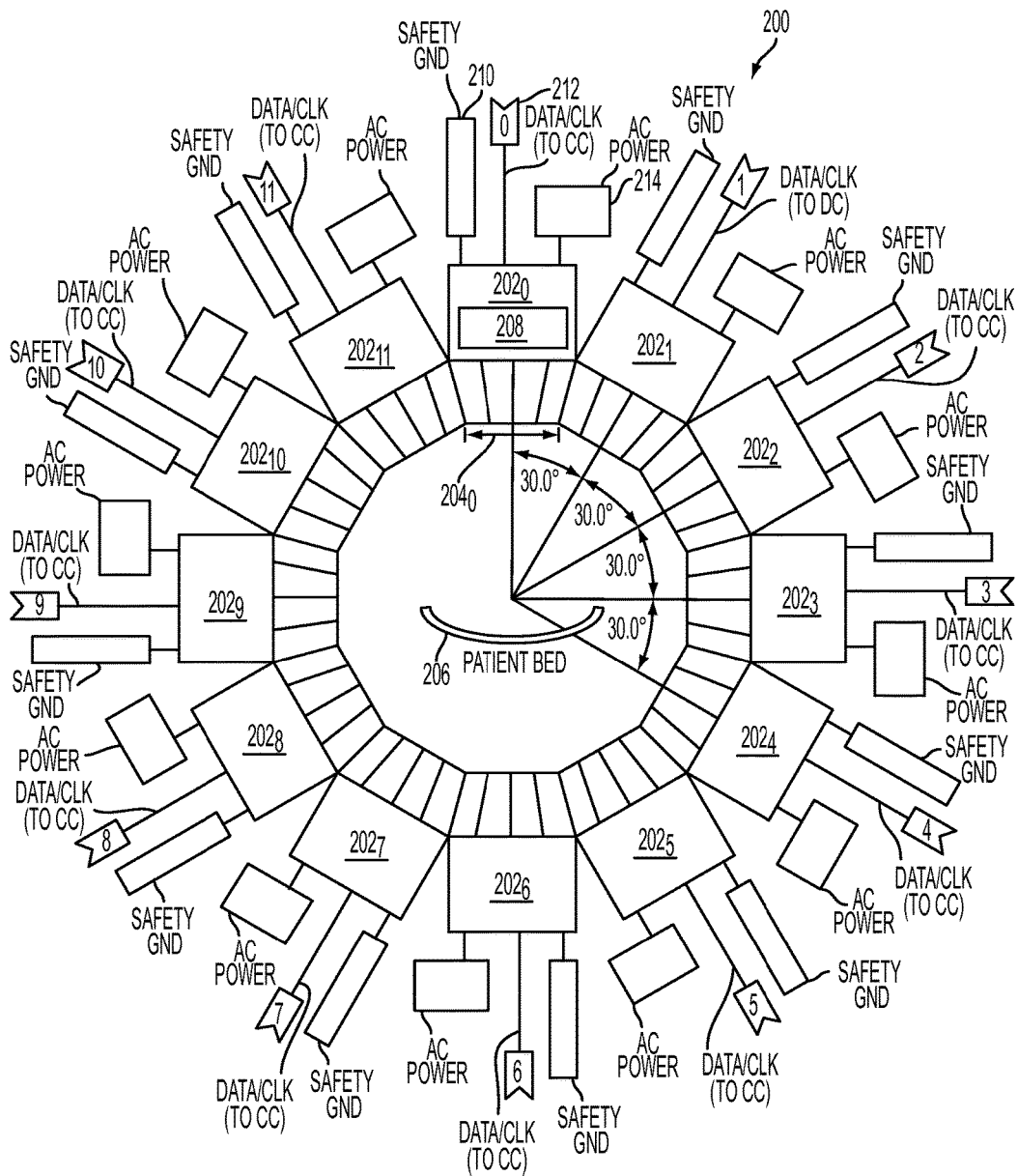
FIG. 2 depicts another schematic view of a detector system in accordance with embodiments of the invention.

FIG. 2 depicts another schematic view of a detector system 200 in accordance with embodiments of the invention. The system 200 includes a ring of immobile detector electronics assembly (DEA $202_0$, DEA $202_1$, DEA $202_2$, DEA $202_3$, DEA $202_4$, DEA $202_5$, DEA $202_6$, DEA $202_7$, DEA $202_8$, DEA $202_9$, DEA $202_{10}$, and DEA $202_{11}$ collectively "DEA units 202").

Each DEA unit 202 includes a safety ground line 210, a data/clock lines 212, and alternating current ("AC") lines 214. For simplicity only, only the safety ground line 210, a data/clock lines 212, and AC lines 214 for the top most DEA unit 202 are depicted in FIG. 2 to include lead lines and numbers.

Illustratively, aspects of the invention are described herein using twelve immobile DEA units 202 that encircle a patient bed 206. However, that depiction is not intended in any way to limit the scope of the invention. For example, it is appreciated and understood that other embodiments of the invention utilize more than one ring of DEA units 202 and that there can be more or less than twelve DEA units 202 in each ring.

Each DEA unit 202 acquires data from a group of detectors 204 (group $204_0$, group $204_1$, group $204_2$, group $204_3$, group $204_4$, group $204_5$, group $204_6$, group $204_7$, group $204_8$, group $204_9$, group $204_{10}$, and group $204_{11}$ (collectively "detectors 204")). The detectors 204 are connected to respective DEA units 202 and provide the field of view ("FOV") of the DEA unit 202 connected thereto. There are twelve groups of detectors 204 (one group for each DEA unit 202).

Both the DEA units 202 and the detectors 204 remain immobile.

Included in each DEA unit 202 is a direct-encoding DC accelerometer 208. For simplicity, FIG. 2 only depicts DEA unit $202_0$ as including an accelerometer 208. However, it is understood that each of the DEA units 202 includes an accelerometer 208.

Each DC accelerometer 208 is broadly referred to as an angular orientation-sensing member. Such accelerometers include a pair of orthogonally arranged sensing elements by which the angle of inclination of the accelerometer relative to Earth's gravitational field can be determined. Accelerometers are typically used to measure motion (by measuring changes in voltage). However, because the DEA units 202 are immobile/stationary fixed DC voltages from the accelerometers are measured and subsequently used to determine the location of the DEA 202 within the ring.

Position information (i.e., at least "X-axis" and "Y-axis" data (and optionally "Z-axis" data (e.g., Z-axis data can be used when the accelerometers 208 are mounted on the detectors 204 to provide the location of a ring))) is compared with data stored in memory (e.g., a look-up table). By comparing the acquired position information with the data stored in memory the angle of inclination of the DEA units 202 are determined. Thus, by measuring the angle of inclination of the DEA unit 202, the location of the DEA unit 202 can be determined, and that location information can be tagged to each event detected by the detector unit, for which the information concerning the detector unit is sent to the imaging system processing computer (not illustrated).

For example, DEA unit $202_0$ has been identified as the top DEA unit (i.e., a DEA unit 202 that is immobile, will always be in the "12 o'clock position" (i.e., will always have an orientation of about 180° with respect to the (i.e., the Earth's gravitational field) and patient bed 206 and will always be downward facing) with respect to the other DEA units 202 in the gantry. Any event that is detected and received by DEA unit $202_0$ is tagged as having come from this top fixed position (again with respect to the other DEA units 202 in the gantry).

When referring to the top most DEA unit 202 as having an orientation of about 180° it is understood that that reference is taken from a central axis of the DEA unit 202. When each DEA unit 202 has a field of view of about 30° then the DEA units 202 adjacent to the top most DEA unit 202 are located at 210° and at 150°.

For example, for a twelve-unit system as shown, the next DEA unit $202_1$ in the clockwise direction will have an orientation of 210° with respect to the ground (i.e., the Earth's gravitational field) and patient bed and other DEA units 202 in the gantry; the next DEA unit $202_2$ will have an orientation of 240° with respect to the ground (i.e., the Earth's gravitational field) and patient bed and other DEA units 202 in the gantry; and so on for all of the DEA units 202 in the scanning system. Thus, the detected events from all DEA units 202 can be compiled along with the associated detector orientations, and the LORs can be generated by pairing essentially simultaneous events that have associated detector orientations that are 180° apart from each other.

The accelerometer can be located anywhere (e.g., on an electronics board or the detectors 204) on the DEA units 202.

In various embodiments of the invention, accelerometer-provided DEA location information is compared to position data stored in memory every time the scanning system is turned "on." One reason for comparing accelerometer-provided DEA locations to position data stored in memory, in those instances when the DEA units 202/detector(s) 204 remain immobile, is that there are instances when the DEA unit(s)/detectors 204 are just installed or swapped to a different location on the gantry.

In other embodiments of the invention, a user can manually actuate (through a user interface) a series of computer instructions that compare the accelerometer-provided DEA locations to position data stored in memory and determines the DEA unit locations on the gantry (relative to the patient bed 206 and the other DEA units on the gantry) based upon the results of the comparison.

In yet other embodiments of the invention, the scanning system periodically (i.e., after expiration of a predetermined time) compares the accelerometer-provided DEA locations to position data stored in memory and determines the DEA unit locations on the gantry (relative to the patient bed 206 and the other DEA units on the gantry) based upon the results of the comparison.

In further embodiments of the invention, the scanning system initiates a series of computer instructions to determine the location of each DEA unit 202 when another program is initiated (e.g., a diagnostic program).

In an alternative arrangement (not illustrated), DEA units 202 unit(s) are provided, which do not completely encircle the patient bed but which are swept around the patient. In this alternative arrangement, the DEA units 202/detectors 204 do not remain immobile/stationary. When more than one DEA unit 202 is provided in the ring each DEA unit 202 has a DEA unit 202 positioned 180° (i.e., oppositely) thereto on the ring. The detector(s) 204/DEA unit 202 in such an arrangement would also include an orientation-sensing accelerometer, by means of which the position in space of the detector 204/DEA unit 202 can be determined and hence the angular location of the detectors 204/DEA unit 202. As with such a system (e.g., a PET system with two opposing detector units), all detected events can be compiled and paired based on opposing detector locations, together with the actual angular orientation of the opposing detectors in space. For example, in a ring having six DEA units 202 (which will begin scanning at predefined positions (e.g., three adjacent DEA units 202 positioned at 330°, 0°, and 30°; and three adjacent DEA units 202 positioned at 150°, 180°, 210°)). When the scanning system is turned "on," the DEA units 202/detectors(s) 204 are stationary and the accelerometers 208 transmit data indicative of the location of the DEA units 202/detector(s) 204. The received data is compared to the predefined locations stored in memory. In various embodiments of the invention, the received data is used to reposition the DEA units 202/detectors(s) 204 to the appropriate angular orientation. In other embodiments of the invention, the data received from the accelerometers 208 is used to replace the predefined locations and is stored in memory.

FIG. 3 depicts an exemplary look-up table 300 in accordance with embodiments of the invention. Although look-up table 300 is depicted as having addresses to accommodate twelve DEA units 202 that depiction is for illustrative purposes only and not intended in any way to limit the scope of the invention. The look-up table 300 includes position data addresses ($302_0$, $302_1$, $302_2$, $302_3$, $302_4$, $302_5$, $302_6$, $302_7$, $302_8$, $302_9$, $302_{10}$, and $302_{11}$ (collectively "position data addresses 302") for storing position data.

Position data is a pre-defined location parameter(s) that identifies locations for the DEA unit 202. For example, when the scanning system includes twelve DEA units 202 it follows that each of the DEA units 202 has a specific location in the ring (i.e., the DEA units 202 are incrementally spread around the ring). As such, there should be a DEA unit 202 located at each of "12:00 o'clock position" (i.e., facing straight down and at 180°) clockwise through to the "11 o'clock position." These positions (i.e., the 12 o'clock position clockwise through 11 o'clock position) are stored in data addresses 302.

As explained above, position information (e.g., at least "X-axis" and "Y-axis" data (and optionally "Z-axis" data)) is received from each of the DEA units 202. This position information, from the DEA units 202, is compared to the position data stored in addresses 302 to determine which DEA unit 202 to associate with each data address 302. The resulting association (of the respective DEA units 202 to data addresses 302) is stored in the look-up table 300 (in addresses $304_0$, $304_1$, $304_2$, $304_3$, $304_4$, $304_5$, $304_6$, $304_7$, $304_8$, $304_9$, $304_{10}$, and $304_{11}$ (collectively "addresses 304")).

In various embodiments, the look-up table 300 optionally includes addresses (e.g., addresses $306_0$, $306_1$, $306_2$, $306_3$, $306_4$, $306_5$, $306_6$, $306_7$, $306_8$, $306_9$, $306_{10}$, and $306_{11}$ for storing X-axis data; addresses $308_0$, $308_1$, $308_2$, $308_3$, $308_4$, $308_5$, $308_6$, $308_7$, $308_8$, $308_9$, $308_{10}$, and $308_{11}$ for storing Y-axis data; and/or addresses $310_0$, $310_1$, $310_2$, $310_3$, $310_4$, $310_5$, $310_6$, $310_7$, $310_8$, $310_9$, $310_{10}$, and $310_{11}$ for storing Z-axis data) for also storing the position information received from the DEA units 302.

Figure 4:
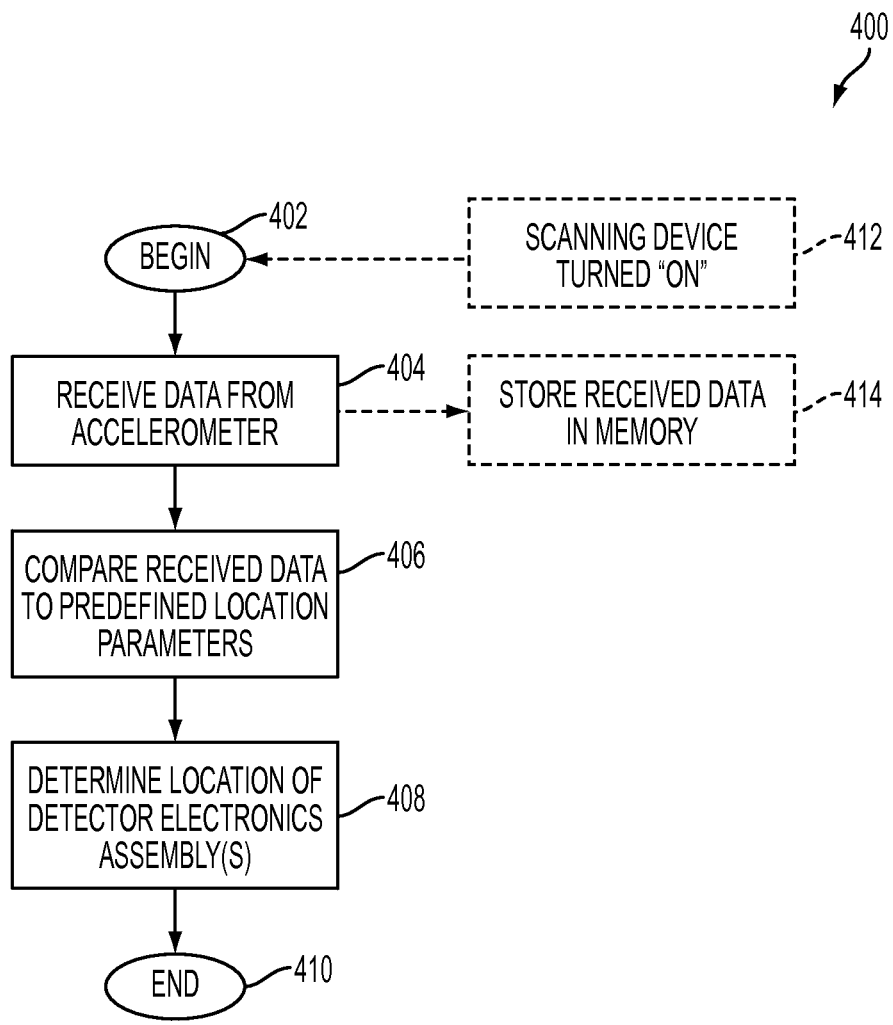
FIG. 4 depicts an exemplary method in accordance with embodiments of the invention.

FIG. 4 depicts an exemplary method 400 in accordance with embodiments of the invention. The method 400 determines the location of DEA units 202. The method 400 begins at step 402 and proceeds to step 404.

At step 404, position information is received from the accelerometers regarding the locations of the DEA units 202. Thereafter, the method 400 proceeds to step 406.

At step 406, the position information is compared to predefined location parameters stored in memory. Thereafter, the method 400 proceeds to step 408.

At step 408, the results of the comparison in step 406, is used to determine the location of the DEA units 202 and store the determination in memory. After step 408, the method 400 proceeds to and ends at step 410.

In various embodiments of the invention, the method 400 includes optional step 412. At optional step 412, the scanning device is turned "on" and in response thereto, the method 400 proceeds to step 402. Step 402 operates as described above.

In yet other embodiments of the invention, the method 400 includes optional step 414. At optional step 414, the position information from the accelerometer 208 is stored in memory (e.g., look-up table 300). Thereafter, the method 400 proceeds to and ends at step 410.

Figure 5:
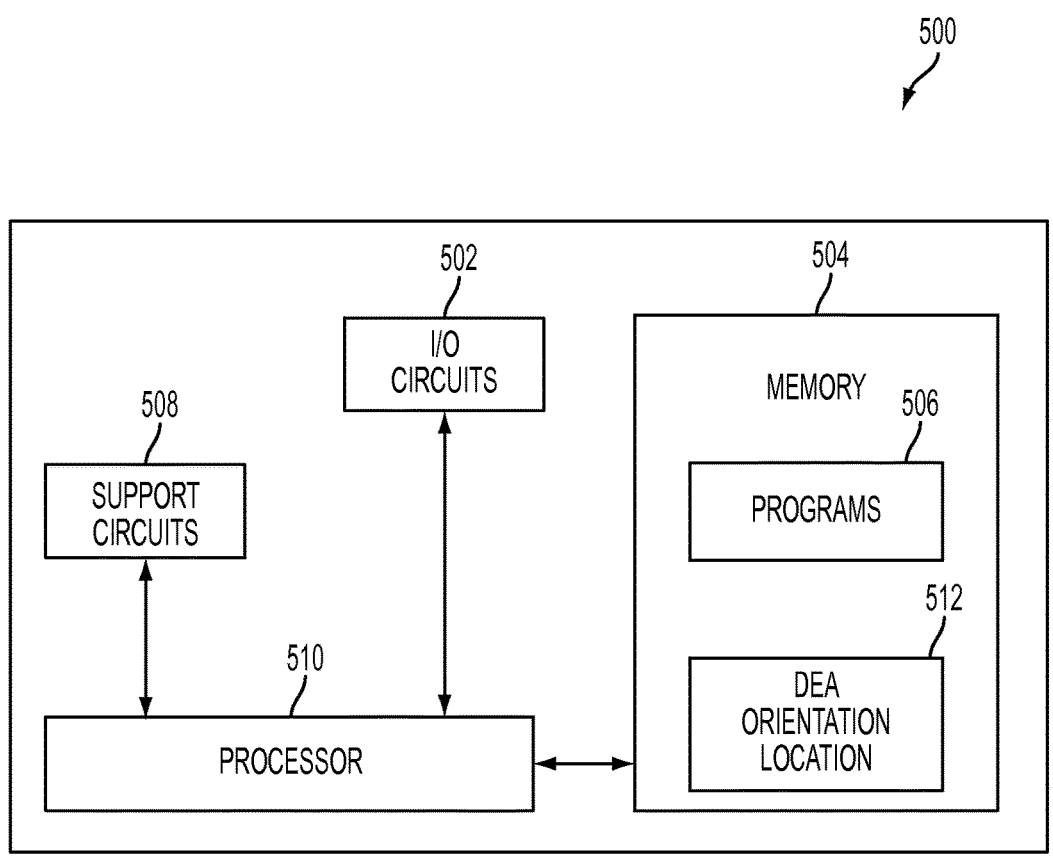
FIG. 5 depicts an embodiment of a high-level block diagram of a computer architecture used in accordance with aspects disclosed herein.

FIG. 5 depicts an embodiment of a high-level block diagram of a general-purpose computer architecture 500 for determining the angular orientation/location of each DEA unit 202 in relation to the other DEA units 202, a patient bed 206, and the ground (i.e., the Earth's gravitational field). For example, the general-purpose computer 500 is suitable for use in performing method 400 (depicted in FIG. 4). The general-purpose computer of FIG. 5 includes a processor 510 as well as a memory 504 for storing control programs and the like. In various embodiments, memory 504 also includes programs 512 (e.g., depicted as a "DEA orientation/location") for determining the angular orientation/location of each DEA unit 202 in a scanner system) for performing the embodiments described herein. The processor 510 cooperates with conventional support circuitry 508 such as power supplies, clock circuits, cache memory and the like as well as circuits that assist in executing the software routines 506 stored in the memory 504. As such, it is contemplated that some of the process steps discussed herein as software processes can be loaded from a storage device (e.g., an optical drive, floppy drive, disk drive, etc.) and implemented within the memory 504 and operated by the processor 510. Thus, various steps and methods of the present invention can be stored on a computer readable medium. The general-purpose computer 500 also contains input-output circuitry 502 that forms an interface between the various functional elements communicating with the general-purpose computer 500.

Although FIG. 5 depicts a general-purpose computer 500 that is programmed to perform various control functions in accordance with the present invention, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. In addition, although one general-purpose computer 500 is depicted, that depiction is for brevity on. It is appreciated that each of the methods described herein can be utilized in separate computers.

Although embodiments of the invention have been described herein as including the accelerometers 208 mounted within the DEA units 202 those descriptions are not intended in any way to limit the scope of the invention. It is appreciated that in other embodiments of the invention the accelerometers 208 are mounted inside/on the detectors 204.

The invention having been thus described, it will apparent to those skilled in the art that the same may be varied in many ways without departing from the spirit and scope of the invention. For example, other imaging technologies besides PET and SPECT may benefit from the invention. Any and all such modifications are intended to be included within the scope of the following claims.

While the foregoing is directed to embodiments of the present invention, other and further embodiments of the invention may be devised without departing from the basic scope thereof, and the scope thereof is determined by the claims that follow.

I claim:

1. A nuclear medical imaging system, comprising:
 a plurality of stationary detector units configured to encircle a patient to be imaged, said plurality of stationary detector units being responsive to radiation photons emitted by a radiopharmaceutically doped organ tissue mass of the patient to output a signal indicative of a radiation photon event;
 a plurality of angular orientation-sensing accelerometers each mounted on a respective stationary detector unit, each of said plurality of angular orientation-sensing accelerometers being configured to provide an angular position of the respective detector unit on which it is mounted, wherein a radiation photon event signal outputted by a stationary detector unit is tagged with a respective angular position provided by a respective angular orientation-sensing accelerometer; and
 an image processor configured to receive radiation photon event signals tagged with angular position information and to use said tagged signals to reconstruct an image of the doped organ tissue mass.

2. The nuclear medical imaging system of claim 1, wherein each angular orientation sensing accelerometer determines the angle of inclination of the respective coupled detector unit relative to the Earth's gravitational field.

3. The nuclear medical imaging system of claim 1, wherein said accelerometer is a DC accelerometer.

4. The nuclear medical imaging system of claim 1, wherein each angular orientation-sensing accelerometer provides address information for communications of said image processor with said detector unit.

5. The nuclear medical imaging system of claim 1 wherein each said angular orientation-sensing accelerometer is further configured to transmit a signal indicative of at least one of a position on an X-axis, a position on a Y-axis, and a position on a Z-axis of said detector units in a predefined three dimensional coordinate system.

6. The nuclear medical imaging system of claim 1, wherein each of said stationary detector units comprises
- a detector electronics assembly (DEA) and a radiation detector array, wherein each array is connected to a respective DEA;
- each angular orientation-sensing accelerometer being connected to a respective DEA.

* * * * *